United States Patent [19]

McLorg

[11] Patent Number: 4,742,826
[45] Date of Patent: May 10, 1988

[54] CICATRISIVE STRIP WITH BIAS

[76] Inventor: Anthony B. McLorg, 746 Chinoe Rd., Lexington, Ky. 40502

[21] Appl. No.: 850,298

[22] Filed: Apr. 7, 1986

[51] Int. Cl.[4] .................. A61B 17/04; A61B 17/06; A61F 13/00

[52] U.S. Cl. ............................ 128/335; 128/155; 206/440

[58] Field of Search ............ 128/335, 155, 156; 206/440, 484, 813; 604/304, 307

[56] References Cited

U.S. PATENT DOCUMENTS

| | | | |
|---|---|---|---|
| 1,969,188 | 7/1934 | Spicer | 128/335 |
| 2,012,755 | 8/1935 | De Muth | 128/335 |
| 2,244,448 | 6/1941 | Eaton | 128/335 |
| 2,421,193 | 5/1947 | Gardner | 128/335 |
| 2,798,492 | 7/1957 | Barnes et al. | 128/335 |
| 2,807,262 | 9/1957 | Lew | 128/156 |
| 3,073,304 | 1/1963 | Schaar | 206/440 |
| 3,520,306 | 7/1970 | Gardner et al. | 128/335 |
| 3,903,335 | 9/1975 | Jones | 206/440 |
| 4,210,148 | 7/1980 | Stivala | 128/335 |
| 4,222,383 | 9/1980 | Schossow | 128/335 |

FOREIGN PATENT DOCUMENTS 488740 12/1952 Canada .................. 206/440

Primary Examiner—Richard C. Pinkham
Assistant Examiner—Gary Jackson
Attorney, Agent, or Firm—King & Schickli

[57] ABSTRACT

A cicatrisive strip suture is formed from an elastic sheet material oriented on a bias so as to provide even compressive forces all along a wound. The sheet material includes a transparent central portion allowing visual alignment of the wound during suture application. Adhesive coated tongues extend outwardly from opposite sides of the central portion to engage the tissue on each side of the wound and hold the suture in proper position. The suture also includes doubled-over backing strips for simple application of the suture to the wound and a sanitary outer wrapper. A sterility bridge formed across the wrapper and suture maintains the sterility of the remaining portion of the suture when a segment of the suture is removed for use.

13 Claims, 3 Drawing Sheets

CICATRISIVE STRIP WITH BIAS

TECHNICAL FIELD

The present invention relates generally to sutures and, more particularly, to a cicatrisive strip suture allowing proper alignment of marginal skin edges during application and providing a noninvasive means of holding a wound closed during healing.

BACKGROUND OF THE INVENTION

A number of suturing techniques to close wounds during healing are well known in the art. These include the use of closure and/or retention sutures of plastic or nylon that are sewn into the skin to bring the marginal edges of the skin around the wound together and hold them in position during healing. An alternative to sewn sutures are staples that extend across the wound at spaced locations along the length of the wound.

It should be recognized that while each of these approaches does effectively hold a wound closed for healing, each suffers from distinct disadvantages as well. Both sewn sutures and staples are invasive techniques that penetrate and damage the interior tissues of the body. Being invasive, these sutures also act as wicks for infection caused by foreign bodies and germs. The use of invasive sutures also prevents effective application of cleansing and healing agents to the wound. Further, in the event infection does develop, the wound may need to be reopened, requiring the painful removal of the invasive sutures and subsequent reclosing with sutures, further damaging the interior body tissues.

While staples may not damage the interior tissues to the extent of sewn sutures, staples do not provide an even closing pressure all along the wound. Rather, staples provide spaced points of localized pressure along the wound that can lead to uneven healing and increased scarring. Further, it should be appreciated that being invasive, both staples and sewn sutures must be removed from the patient before the skin tissues completely heal around them. Such early removal makes it necessary to provide some closing pressure to the wound as a prophylaxis to prevent rupture or reopening.

Recognizing the shortcomings of invasive suturing techniques, butterfly sutures including adhesive strips placed across the wound have been more recently developed. These noninvasive sutures avoid any damage to the interior tissues as well as the wicking action that may lead to infection. Still, with past adhesive strip sutures it has been difficult to properly align the skin margins around the wound during application. Further, past noninvasive sutures have suffered from an inability to protect the wound from opening when subjected to shear loading as may occur during certain body movements. They have also failed to allow the application of cleansing and healing agents to the wound as may be desired. A need is, therefore, identified for an improved noninvasive strip suture.

SUMMARY OF THE INVENTION

Accordingly, it is a primary object of the present invention to provide an improved noninvasive strip suture overcoming the above-described limitations and disadvantages of the prior art.

Another object of the present invention is to provide an improved strip suture allowing visual alignment of the marginal skin edges during suture application and furnishing even compressive forces all along the wound so as to minimize scarring.

Still another object of the present invention is to provide a cicatrisive strip suture constructed to resist shear loading along a wound and maintain the wound closed during healing.

A further object of the present invention is to provide a strip suture allowing the application of air and light as well as cleansing and healing agents to the wound without the wicking action that can lead to infection.

Still another object of the present invention is to provide a strip suture in roll form that is specially wrapped to maintain sterility until use.

An additional object of the present invention is to provide a noninvasive suture constructed to be easily manipulated to follow a wound line as well as to resist peeling.

Additional objects, advantages and other novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

To achieve the foregoing and other objects, and in accordance with the purposes of the present invention as described herein, an improved noninvasive strip suture is provided for spanning a wound and holding the wound closed during healing. The suture includes a central portion for overlying the wound and means, such as adhesive-backed tongues, for releasably securing the suture in position. Specifically, one securing tongue projects from each of two opposite sides of the central portion of the suture. When applied to a wound, the opposing tongues are stretched apart and one tongue is adhesively fixed to the skin on each side of the wound so that the central portion of the suture overlies and protects the wound.

The suture is formed from an elastic sheet material, such as vinyl. The elastic sheet material is oriented on a bias so as to advantageously provide even compressive forces all along the wound for rapid, substantially scar-free healing. The bias orientation further serves to resist wound opening even when the wound is subjected to shear loading.

Preferably, the central portion of the suture is substantially transparent so as to allow accurate, visual alignment of the wound edges during suture application. To further aid in this alignment, the transparent elastic material may be formed with ridges which are substantially convex in cross-section. The suture then acts as a lens that magnifies the wound thereby allowing the skin margins around the wound to be brought into better approximation. Of course, since cells identify themselves by their progenerative neighbors, the better the approximation, the more rapid and scar free the healing. As a further advantage, the convex cross-section also resists the accidental peeling of the suture from the skin. This feature assures that the wound is subjected to the desired wound closing pressure for the entire treatment period until the suture is removed by the attending physician.

More specifically, the elastic sheet material of the suture includes aligned diamond-shaped openings. These openings not only form the diagonal or bias grid structure of the suture but allow air and light to reach the wound and promote healing. The application of cleansing and healing agents, such as vitamin E, to the wound is also possible. Since the suture is noninvasive, no wicking occurs resulting in infection. Further, the raised ridges of elastic sheet material between the openings of the central portion of the suture protect the wound from direct contact with, for example, an overlying shirt worn by the patient. Thus, the suture of the present invention avoids this additional irritation to the wound.

The suture is packaged with backing strips overlying and protecting the adhesive coating on each tongue until use. Preferably, the backing strips are doubled over to provide a free end extending past the distal end of each tongue. Thus, as the tongues are pulled in opposite directions to stretch the elastic material, the backing strips may be easily removed so as to adhesively fix the suture to the skin in a position spanning the wound. Such application assures that the necessary wound closing pressure is provided all along the length of the wound.

The suture is also enclosed in a sealed, sanitary outer wrapper to insure sterility prior to use. Both the backing strips and the outer wrapper may be formed from polyethylene or other similar plastic material.

In accordance with a further aspect of the present invention, the suture may be formed in a roll with a substantially continuous central portion and a series of spaced tongues as described above. When provided in roll form, a segment of suture is cut to substantially match the length of the wound to be closed but allowing for some overlap at the wound ends. The remaining portion of the suture is maintained sterile by a sterility bridge formed across and in the outer wrapper at the spaces between the tongues. The sterility bridge is preferably in the form of a heat seal line wherein the sanitary wrapper is heat welded together across the suture.

Still other objects of the present invention will become readily apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modifications in various, obvious aspects all without departing from the invention. Accordingly, the drawing and descriptions will be regarded as illustrative in nature and not as restrictive.

BRIEF DESCRIPTION OF THE DRAWING

The accompanying drawing incorporated in and forming a part of the specification, illustrates several aspects of the present invention, and together with the description serves to explain the principles of the invention. In the drawing.

Reference will now be made in detail to the present preferred embodiment of the invention, an example of which is illustrated in the accompanying drawing.

DETAILED DESCRIPTION OF THE INVENTION

Reference is now made to FIGS. 1–4 showing the cicatrisive strip suture 10 of the present invention for spanning a wound and holding the wound closed during healing. The suture 10 is formed from a transparent elastic sheet material such as vinyl. The elastic sheet material is oriented on a bias so that the suture 10 resists the tendency of shear loading along the wound to open the wound and cause secondary rupture.

Specifically, aligned diamond-shaped openings 11 provided in the sheet material form the diagonal grid structure of the suture 10. When positioned over the wound, the elastic material in the grid structure extends continuously across the wound only at angles of substantially 45° with respect to the wound line. This results in the application of even compressive forces all along the wound line rather than points of stress concentration in the area between the opposing tongues as with prior art sutures. Further, the aligned diamond-shaped openings 11 allow the application of cleansing and healing agents to the wound.

Figure 4:
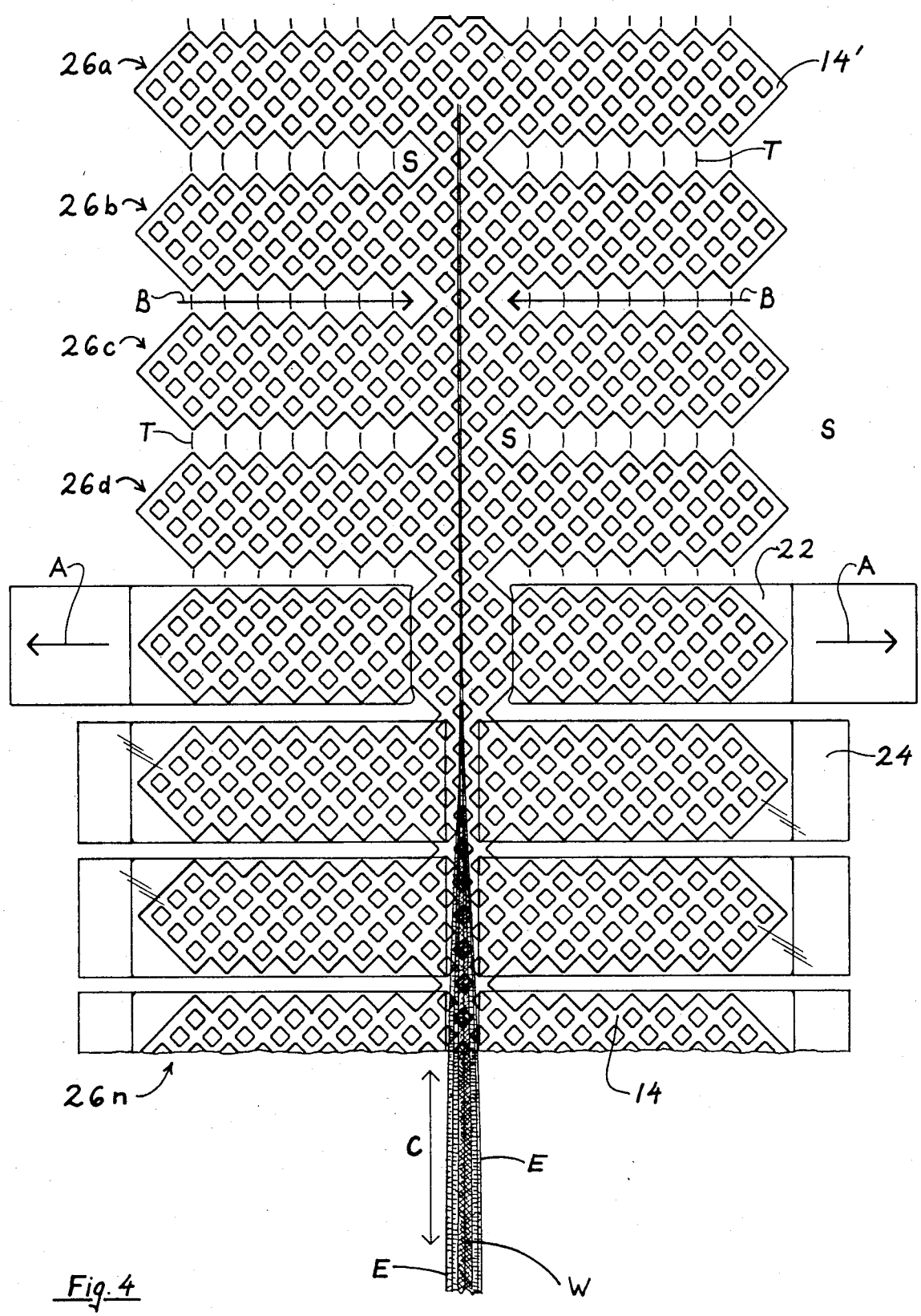
FIG. 4 is a top plan view of a suture of the present invention being applied to a wound.

The suture 10 includes a central portion 12 that is positioned so as to overlie and protect the wound W, as shown in FIG. 4. Securing tongues 14 extend from each side of the central portion 12. The backing or under surfaces of each securing tongue 14 includes a coating of pressure sensitive adhesive 16. Thus, the tongues 14 with the adhesive backing effectively adhere the suture 10 to the skin S around the wound W and maintain the suture in proper position throughout the healing period.

Figure 2:
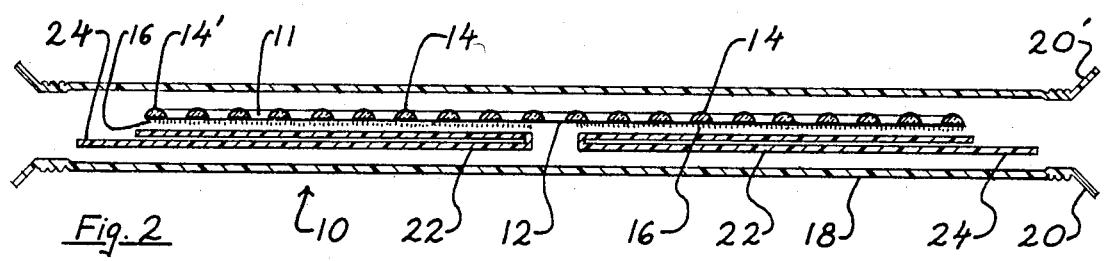
FIG. 2 is a cross-sectional view (slightly exploded for clarity) along line 2—2 of FIG. 1 through an individual suture unit.

The suture 10 is packaged in a sanitary outer wrapper 18 of clear polyethylene or other plastic to maintain sterility prior to use. As shown in FIG. 2, the outer wrapper 18 comprises upper and lower plastic sheets having marginal edges 20, 20' that are heat sealed together as, for example, by heated pressure rollers.

Backing strips 22, also of polyethylene or other plastic, are provided facing the adhesive coating 16 of each tongue 14. The backing strips 22 protect the adhesive properties of the coating 16 until the packaging is opened, discarded and the strips are then removed for application of the suture 10 to a wound. Each backing strip 22 is doubled over to provide a free end 24 extending beyond the distal end 14' of each tongue 14. The free ends 24 may be easily grasped by an individual to apply the suture 10 to a wound W without any loss of sterility and with the proper wound closing tension as discussed in greater detail below.

Figure 1:
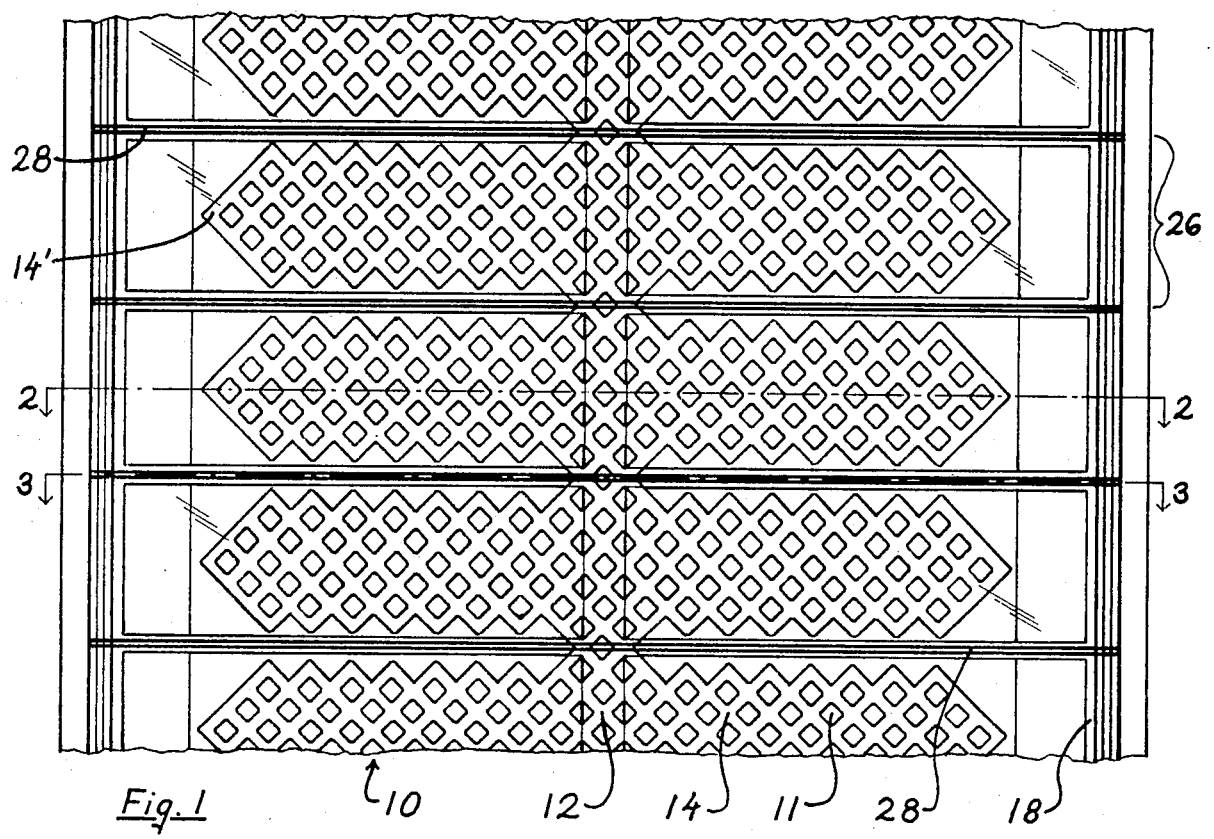
FIG. 1 is a broken away top plan view of the suture of the present invention showing a number of individual suture units connected together in continuous fashion.
Figure 3:
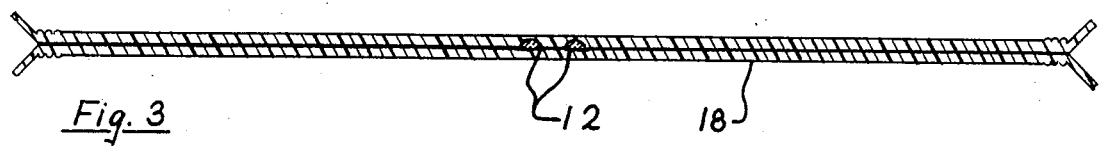
FIG. 3 is a cross-sectional view along line 3—3 of FIG. 1 through a heat sealed sterility bridge provided between individual suture units.

For user convenience, as well as structural continuity, the suture 10 may be formed as a substantially continuous roll including a number of individual suture units 26 in series (note FIG. 1). A segment of the suture 10 of sufficient length to cover a wound may then be simply cut from the roll (not shown) as required. A sterility bridge 28 between the spaced tongues 14 maintains the sterility of the remaining suture 10 in the roll. The sterility bridge 28 comprises a heat sealed line extending across the suture 10 between the heat sealed marginal edges 20, 20' at each side of the wrapper 18. As shown in FIG. 3, the heat sealing serves to weld or melt the upper and lower sheets of the outer wrapper 18 together tightly around the central portion 12 of the suture 10 to form a sanitary barrier.

Simple visual inspection allows a determination of the integrity of the sterility bridge 28 and sanitary outer wrapper 18. Clarity and taut smoothness within an individual unit 26 indicates sterility. Conversely, if the unit 26 appears cloudy or puffy on visual inspection, air or moisture has entered the individual unit through an opening in the outer wrapper 18 or seam in the sterility bridge 28 and the suture is not sterile.

As briefly indicated above, the suture 10 of the present invention is particularly easy to use. The suture 10 is unrolled and cut into a segment of the desired length to cover the wound with some overlap at each end. The suture 10 is then carefully removed from the sanitary outer wrapper 18 by grasping the marginal edges 20, 20' and pulling them apart. The entire segment of the suture 10 including backing strips 22 is then positioned over the wound W with the ends of the suture extending past the end of the wound (note suture unit 26a in FIG. 4). The suture unit 26a at one end of the wound is applied first. The free ends 24 of the backing strips 22 and the distal ends 14' of the tongues 14 are grasped together. The tongues 14 and backing strips 22 are then pulled outwardly (note action arrows A) from the central portion 12 of the strip 10 in opposite directions.

As this is done, the central portion 12 of the suture 10 is maintained over the wound W and the marginal edges of the wound are visually aligned. This is possible since the suture 10 is transparent. Further, where the raised ridges between openings 11 are formed with a convex cross-section as shown in FIG. 2, the suture acts as a magnifying lens allowing still more accurate visual alignment of the wound edges E.

Once the wound edges E are properly aligned, the free ends 24 of the backing strips 22 are pulled outwardly (again, note action arrows A) while maintaining the tongues 14 under pressure. This serves to peel the backing strips 22 from the adhesive 16 on the bottom of the tongues 14 thereby bringing the adhesive into contact with the underlying skin S alongside the wound W. After removal of the backing strips 22, the suture 10 is secured to the skin S bordering the wound W.

Following application of the first suture unit 26a, the second 26b, third 26c, fourth 26d, . . . nth 26n suture units are serially applied in the same manner described above. When finally applied to the full length of the wound W, the suture 10 of the present invention provides an even compressive force all along the wound (note action arrows B and tension lines T in skin S in FIG. 4) to maintain the aligned wound edges closed for rapid, substantially scar-free healing. The compressive force is the result of the suture 10, stretched outwardly during application to the wound W, seeking to return to its original shape.

Further, it should be appreciated that since the suture 10 is resilient, it provides this wound closing pressure for as long as it is maintained in position spanning the wound W. Since the suture 10 is noninvasive, there is no need to remove it prior to full healing as may be necessary with staples or stitching. Thus, wound closing pressure may be provided throughout the entire healing process substantially reducing any possibility of wound rupture.

In summary, numerous benefits result from employing the concepts of the present invention. The suture 10 may be easily packaged in a roll for user convenience. The sterility of the suture 10 remaining on the roll following use is simply maintained by a sterility bridge 28 extending across the suture between the spaced tongues 14. The suture 10 also advantageously provides even compressive forces all along the wound to promote rapid healing with minimum scarring. Unlike with staples as used in the prior art, the skin adjacent the wounds is not loaded with points of stress concentration that distort the geometry of the healing process. The bias orientation of the suture 10 also resists wound opening even when the wound is subjected to shearing loads. Further, the diamond-shaped openings 11 in the suture 10 allow the application of cleansing and healing agents to the wound to speed the healing process. Since the suture 10 is noninvasive there is no wicking action to cause infection and no additional damage to the underlying tissues characteristic of invasive sutures.

Figure 5:
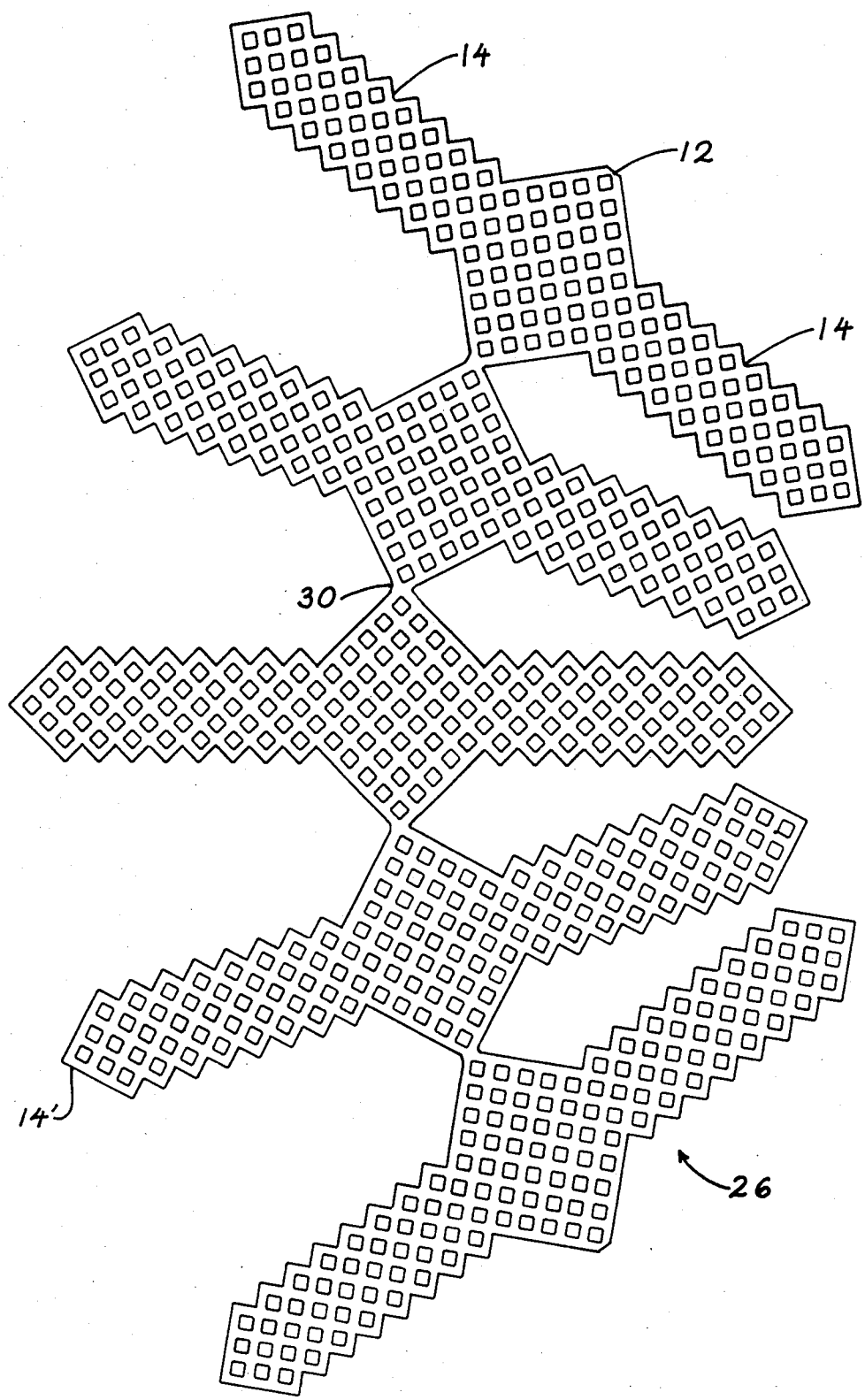
FIG. 5 is a top plan schematic view showing an alternative embodiment and how the suture can be made to follow a curved wound path.

The foregoing description of a preferred embodiment of the invention has been presented for purposes of illustration and description. It is not intended to be exhaustive or to limit the invention to the precise form disclosed. Obvious modifications or variations are possible in light of the above teachings. For example, the grid gauge of the elastic suture material may be varied to suit different stress and curvature requirements characteristic of the wound in question. Further, as shown in the alternative embodiment of FIG. 5, the central portion 12 of the suture 10 may be narrowed as, for example, at 30 to allow easier orientation of the suture to follow curved wounds. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

I claim:

1. A cicatrisive strip suture for spanning a wound and holding a wound closed during healing, comprising:
   an elastic sheet material including a central portion for overlying the wound and means for releasably securing said suture to tissue on opposite sides of said wound; said securing means including a pair of tongues projecting from opposite sides of said central portion, said tongues including an adhesive coating for engaging tissue on each side of said wound and holding said suture in position to close said wound; said suture further including backing strips, one backing strip facing the adhesive coating of each tongue to protect the adhesive until use, each of said backing strips being doubled over to provide a free end extending from a distal end of each tongue thereby allowing simple application of said suture to said wound.

2. The suture of claim 1, wherein said suture includes a sanitary outer wrapper.

3. The suture of claim 2, wherein said backing strips and wrapper are formed of polyethylene.

4. The suture of claim 1, wherein said suture includes a substantially continuous central portion and a series of spaced tongues for releasably securing said suture to tissue on each side of said wound.

5. The suture of claim 4, wherein said central portion is narrowed between said tongues so that said suture may be easily oriented to follow said wound.

6. The suture of claim 1, wherein said suture includes a sanitary outer wrapper.

7. The suture of claim 6, further including sterility bridge means across said wrapper in the spaces between said tongues, said sterility bridge means serving to maintain the sterility of remaining suture after a segment of said suture is removed for use.

8. The suture of claim 7, wherein said sterility bridge means is a heat sealed line wherein said sanitary wrapper is melted together across said suture.

9. A cicatrisive strip suture for spanning a wound and holding a wound closed during healing, comprising:
an elastic sheet material including a central portion for overlying the wound and means for releasably securing said suture to tissue on opposite sides of said wound; said elastic sheet material having raised ridges at least in said central portion, said ridges being substantially convex in cross-section so as to resist peeling and said central portion being substantially transparent so as to form a lens to magnify the wound for better alignment of the wound edges during suture application.

10. The suture of claim 9, wherein aligned diamond-shaped openings are provided all along said elastic sheet material to form said bias and provide access to the wound for the application of air, light, cleansing and healing agents.

11. The suture of claim 9, wherein said elastic sheet material is substantially transparent vinyl.

12. The suture of claim 9, further including backing strips, one backing strip overlying the adhesive coating of each tongue to protect the adhesive until use.

13. The suture of claim 12 wherein each of said backing strips is doubled over to provide a free end extending from a distal end of each tongue thereby allowing simple application of said suture to said wound.

* * * * *